(12) United States Patent
Wingen et al.

(10) Patent No.: US 6,465,060 B1
(45) Date of Patent: Oct. 15, 2002

(54) TETRAHYDROTHIOPHENE DERIVATIVES, AND THEIR USE IN LIQUID-CRYSTALLINE MIXTURES

(75) Inventors: Rainer Wingen, Hattersheim (DE); Barbara Hornung, Hasselroth (DE); Wolfgang Schmidt, Dreieich (DE)

(73) Assignee: Clariant International Ltd., Mutenz (CH)

( * ) Notice: Subject to any disclaimer, the term of this patent is extended or adjusted under 35 U.S.C. 154(b) by 143 days.

(21) Appl. No.: 09/708,852

(22) Filed: Nov. 7, 2000

(30) Foreign Application Priority Data

Nov. 9, 1999 (DE) .......................... 199 53 804

(51) Int. Cl.$^7$ ...................... C09K 19/34; C07D 333/02; C07D 333/06
(52) U.S. Cl. ...................... 428/1.1; 252/299.61; 549/62; 549/65; 549/66; 549/67; 549/72
(58) Field of Search .................... 252/299.61, 299.1; 428/1.1; 549/62, 74, 65, 66, 67

(56) References Cited

FOREIGN PATENT DOCUMENTS

| | | |
|---|---|---|
| DE | 19748432 | 5/1999 |
| EP | 0500072 | 8/1992 |
| EP | 364923 | 7/1993 |
| EP | 0916714 | 5/1999 |
| JP | 5-239069 | * 9/1993 |

OTHER PUBLICATIONS

English abstract of JP 05–239069, 1993.*

* cited by examiner

*Primary Examiner*—Shean C. Wu

(74) *Attorney, Agent, or Firm*—Frommer Lawrence & Haug LLP

(57) ABSTRACT

Tetrahydrothiophene derivatives of the formula (I)

$$R^1\text{—}X\text{—}(A^1\text{—}M^1)_a\text{—}(A^2\text{—}M^2)_b\text{—}A^3\text{—}Y\text{—}T\text{—}Z\text{—}R^2 \qquad (I)$$

where the symbols and indices have the following meanings, for example:

T is undirected and is tetrahydrothiophene-2,5-diyl or tetrahydrothiophene-2,4-diyl $R^1$ is hydrogen or a straight-chain or branched $C_{1-20}$-alkyl or $C_{2-20}$-alkenyl radical (with or without asymmetric carbon atoms), $R^2$ is hydrogen or a straight-chain or branched alkyl radical (with or without asymmetric carbon atoms) having 1 to 20 carbon atoms, X is a single bond, —O—, OC(=O)—, —C(=O)O— or —OC(=O)O—

Y is —OC(=O)—, —SC(=O)—, —OCH$_2$— or —CH$_2$CH$_2$—

Z is a single bond or —O—

$A^1$, $A^2$ and $A^3$ are undirected different and are each, independently of one another phenylene-1,4-diyl, $M^1$ and $M^2$ are undirected and are each, independently of one another —OC(=O)—, —OCH$_2$—, —CH$_2$CH$_2$—, —OC(=O)CH$_2$CH$_2$—, —OCH$_2$CH$_2$CH$_2$—, —C≡C—, —CH$_2$CH$_2$CH$_2$CH$_2$— or a single bond;

a and b are each, independently of one another, 0 or 1, can be used in liquid-crystal mixtures.

7 Claims, No Drawings

TETRAHYDROTHIOPHENE DERIVATIVES, AND THEIR USE IN LIQUID-CRYSTALLINE MIXTURES

BACKGROUND OF THE INVENTION

1. Field of the Invention

Besides nematic and cholesteric liquid crystals, optically active, tilted, smectic (ferroelectric) liquid crystals have also recently been used in commercial display devices.

2. Description of Related Art

Clark and Lagerwall have been able to show that the use of ferroelectric liquid crystals (FLCs) in very thin cells results in opto-electrical switching or display elements which have response times which are faster by a factor of up to 1000 compared with conventional TN ("twisted nematic") cells (see, for example, EP-A 0 032 362). Owing to this and other favorable properties, for example the possibility of bistable switching and the virtually viewing angle-independent contrast, FLCs are basically highly suitable for areas of application such as computer displays.

For a more detailed explanation of the technical requirements of FLCs, reference is made to European Patent Application 0 916 714 and DE-A 197 48 432.

Thiophene derivatives have already been described for use in liquid-crystal mixtures, for example in EP-B-0 364 923 or 0 500 072.

However, since the development, in particular of ferroelectric liquid-crystal mixtures, can in no way be regarded as complete, display manufacturers are interested in a wide variety of components for mixtures, partly because only the interaction of the liquid-crystalline mixtures with the individual components of the display device or of the cells (for example the alignment layer) allows conclusions to be drawn on the quality of the liquid-crystalline mixtures too.

BRIEF SUMMARY OF THE INVENTION

It has now been found that tetrahydrothiophene derivatives of the formula (I), even when admixed in small amounts, have a favorable effect on the properties of liquid-crystal mixtures, in particular chiral smectic mixtures, for example regarding the dielectric anisotropy and/or the melting point, but also regarding the switching behavior, the tilt angle values and the temperature dependence of the tilt angle.

DETAILED DESCRIPTION OF THE INVENTION

The invention therefore provides tetrahydrothiophene derivatives of the formula (I)

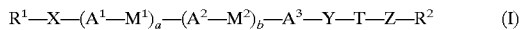

$$R^1-X-(A^1-M^1)_a-(A^2-M^2)_b-A^3-Y-T-Z-R^2 \quad (I)$$

where the symbols and indices have the following meanings:

T is undirected and is tetrahydrothiophene-2,5-diyl or tetrahydrothiophene-2,4-diyl $R^1$ is hydrogen or a straight-chain or branched $C_{1-20}$-alkyl or $C_{2-20}$-alkenyl radical (with or without asymmetric carbon atoms), where a) one or two nonterminal $CH_2$ groups may be replaced, independently of one another, by —O— or —C(=O)—, with the proviso that two adjacent $CH_2$ groups cannot be replaced in the same way, and/or b) one $CH_2$ group may be replaced by —C≡C—, and/or c) one $CH_2$ group may be replaced by —Si($CH_3$)$_2$—, cyclopropane-1,2-diyl, cyclobutane-1,3-diyl, cyclopentane-1,4-diyl, bicyclo[1.1.1]pentane-1,3-diyl or cyclohexane-1,4-diyl, and/or d) one or more H atoms may be replaced by F and/or CN, e) in the case of an alkyl or alkenyl radical containing asymmetric carbon atoms, the asymmetric carbon atoms have —$CH_3$, —$OCH_3$, —$CF_3$, F, CN and/or Cl as substituents or are incorporated into a 3- to 7-membered ring, in which, in addition, one or two non-adjacent $CH_2$ groups may be replaced by —O— and one $CH_2$ group non-adjacent to these groups may be replaced by —OC(=O)—;

$R^2$ is hydrogen or a straight-chain or branched alkyl radical (with or without asymmetric carbon atoms) having 1 to 20 carbon atoms, where one nonterminal $CH_2$ group may be replaced by —O— or —OC(=O)— or —C(=O)O— and/or one or more H atoms may be replaced by F, with the provisos that a) the $CH_2$ group attached to Z cannot be replaced by —O— when Z is —O— b) $R^2$ can only be hydrogen when Z is a single bond and $R^1$ is not hydrogen

X is a single bond, —O—, OC(=O)—, —C(=O)O— or

Y is —OC(=O)—, —SC(=O)—, —$OCH_2$— or —$CH_2CH_2$—

Z is a single bond or —O—

$A^1$, $A^2$ and $A^3$ are undirected and are each, independently of one another phenylene-1,4-diyl, unsubstituted or monosubstituted or disubstituted by CN or F, phenylene-1,3-diyl, unsubstituted or monosubstituted or disubstituted by CN or F, cyclohexane-1,4-diyl, in which one or two H atoms may be replaced, independently of one another, by CN, $CH_3$ or F, 1-cyclohexene-1,4-diyl, in which one H atom may be replaced by F, 1-alkyl-1-silacyclohexane-1,4-diyl, pyridine-2,5-diyl, unsubstituted or monosubstituted by F, pyrimidine-2,5-diyl, unsubstituted or monosubstituted by F, thiophene-2,5-diyl or (1,3,4)-thiadiazol-2,5-diyl $M^1$ and $M^2$ are undirected and are each, independently of one another —OC(=O)—, —$OCH_2$—, —$CH_2CH_2$—, —$OC(=O)CH_2CH_2$—, —$OCH_2CH_2CH_2$—, —C≡C—, —$CH_2CH_2CH_2CH_2$— or a single bond;

a and b are each, independently of one another, 0 or 1.

"Terminal" means, for example in $R^1$, the $CH_2$ groups connected to X or to H. "Undirected" means that incorporation of the group in the form of its mirror image is possible.

Preference is given to the following compounds of the formulae (I-1) to (I-1 5):

(I-1)

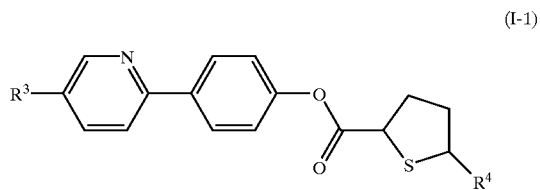

(I-2) 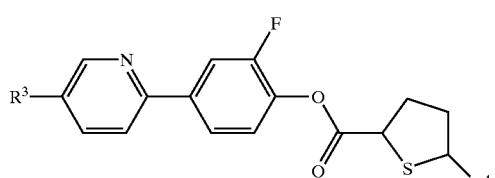

(I-3) 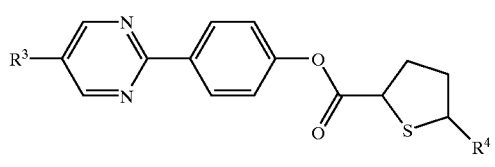

(I-4) 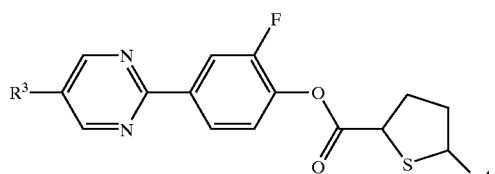

(I-5) 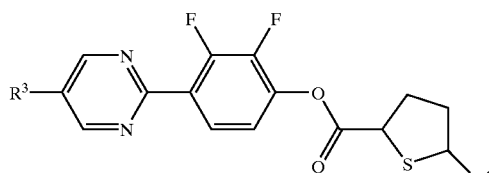

(I-6) 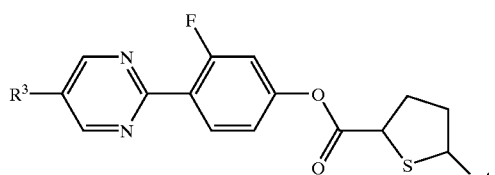

(I-7) 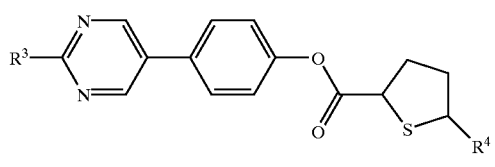

(I-8) 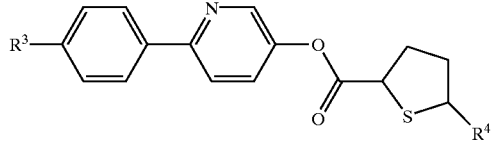

(I-9) 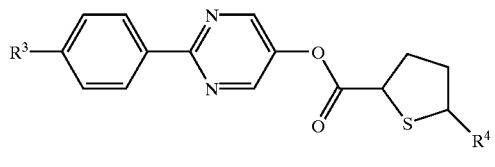

(I-10) 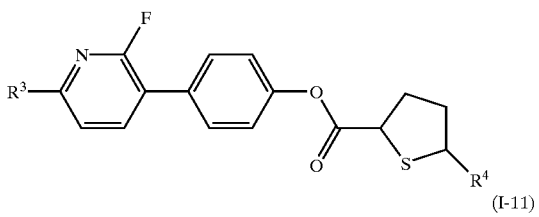

(I-11) 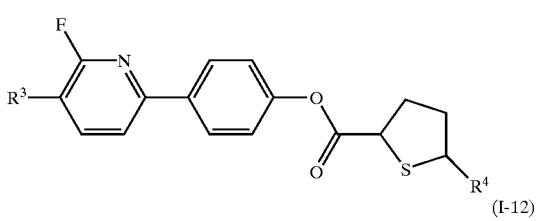

(I-12) 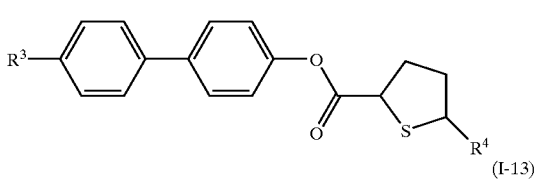

(I-13) 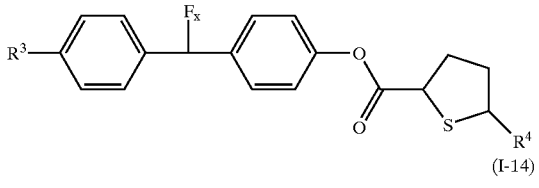

(I-14) 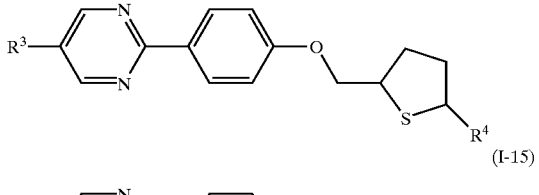

(I-15) 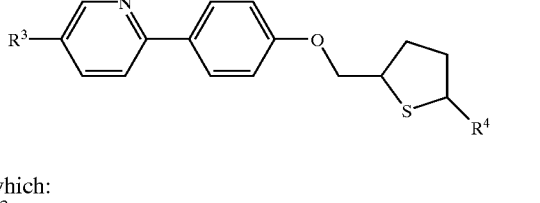

in which:
$R^3$ is hydrogen or a straight-chain or branched alkyl radical (with or without asymmetric carbon atoms) having 1 to 16 carbon atoms, in which, in addition, one nonterminal CH$_2$ group may be replaced by —O— or, undirected, by —OC(=O)— and in which one or more H atoms may be replaced by F;

$R^4$ is hydrogen or a straight-chain or branched alkyl radical (with or without asymmetric carbon atoms) having 1 to 16 carbon atoms, $F_x$ denotes a substitution of the biphenyl by one or two (adjacent) F atoms.

Particular preference is given to compounds of the formulae (I), in particular (I-1) to (I-15), in which $R^3$ and $R^4$ are each, independently of one another, a straight-chain alkyl radical having 2 to 16 carbon atoms.

Particular preference is likewise given to compounds of the formula (I), in particular (I-1) to (I-15), in which $R^3$ is a straight-chain alkoxy radical having 2 to 12 carbon atoms and $R^4$ is hydrogen or a straight-chain alkyl radical having 2 to 12 carbon atoms.

Of the compounds of the formula (I) which are to be used as optically active components (dopants) in liquid-crystal mixtures, preference is given to those in which the alkyl group contains the asymmetric carbon atoms in the form of at least one of the following groups:

a) —C*H(CH$_3$)C$_m$H$_{2m+1}$, where m has a value of from 2 to 8
b) —OC*H(CH$_3$)C$_m$H$_{2m+1}$, where m has a value of from 2 to 8
c) —OC*H(CH$_3$)CO$_2$C$_m$H$_{2m+1}$, where m has a value of from 1 to 10
d) —OC(=O)C*H(CH$_3$)OC$_m$H$_{2m+1}$, where m has a value of from 1 to 10
e) —OC(=O)C*H(F)C$_m$H$_{2m+1}$, where m has a value of from 1 to 10
f) —OCH$_2$C*H(F)C$_m$H$_{2m+1}$, where m has a value of from 1 to 10
g) —OCH$_2$C*H(F)C*H(F)C$_m$H$_{2m+1}$, where m has a value of from 1 to 10
h) oxirane-2,3-diyl in which C* denotes the asymmetric carbon atom.

The compounds according to the invention are prepared by methods known per se from the literature, as described in standard works on organic synthesis, for example Houben-Weyl, Methoden der organischen Chemie [Methods of Organic Chemistry], Georg-Thieme-Verlag, Stuttgart.

However, it may prove necessary to vary or modify the literature methods for the requirements of mesogenic units, since, for example, functional derivatives having long (>C$_6$) alkyl chains tend to be less reactive than, for example, the methyl or ethyl analogues.

Particular reference is made in this connection to the following synthesis schemes, in which the synthesis of the tetrahydrothiophene derivatives of the invention is illustrated in more detail by way of example.

Scheme 1

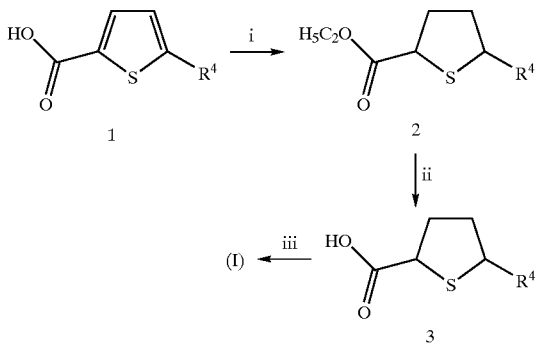

i: 1. Na(Hg), H$_2$O 2. HCl, C$_2$H$_5$OH as described in D. J. Gram, J.Am.Chem.Soc. 89, 4651 (1967).
ii: 1. NaOH 2. HCl
iii: R$^1$—X—(A$^1$—M$^1$)$_a$—(A$^2$—M$^2$)$_b$—A$^3$—OH, DCC/CH$_2$Cl$_2$ The 5-alkylthiophene-2-carboxylic acids 1 required for the synthesis of Scheme 1 are prepared according to the method described in EP-B-0 364 923.

As far as the linking of functional derivatives of the tetrahydrothiophenes with other liquid-crystal-specific units is concerned, express reference is made to DE-A 197 48 432, which gives a list of methods customary to the person skilled in the art.

The invention further provides the use of compounds of the formula (I) in liquid-crystal mixtures, preferably smectic and nematic liquid-crystal mixtures, particularly preferably chiral smectic (ferroelectric) liquid-crystal mixtures. Particular preference is given to the use in ferroelectric liquid-crystal mixtures operated in inverse mode or in switching and display devices having active matrix elements.

Very particular preference is given to the use in mixtures for active matrix LCDs (switching and display devices) in which the chiral smectic liquid-crystal layer forms a monostable-switching monodomain.

The invention furthermore provides liquid-crystal mixtures, preferably smectic and nematic liquid-crystal mixtures, particularly preferably ferroelectric (chiral smectic) liquid-crystal mixtures, which comprise one or more compounds of the formula (I).

The liquid-crystal mixtures according to the invention generally comprise from 2 to 35 components, preferably from 2 to 25 components, particularly preferably from 2 to 20 components.

They generally comprise from 0.01 to 80% by weight, preferably from 0.1 to 60% by weight, particularly preferably from 0.1 to 30% by weight, based on the entire mixture, of one or more, preferably from 1 to 10, particularly preferably from 1 to 5, very particularly preferably from 1 to 3, compounds of the formula (I) according to the invention.

Further components of liquid-crystal mixtures which comprise compounds of the formula (I) according to the invention are preferably selected from known compounds having smectic and/or nematic and/or cholesteric phases. Further mixture components which are suitable in this context are listed, in particular, in international patent application WO 97/04039 and in DE-A 197 48 432, which are incorporated herein by reference.

The mixtures according to the invention can in turn be used in electro-optical or fully optical elements, for example display elements, switching elements, light modulators, elements for image processing and/or signal processing, or generally in the area of nonlinear optics.

The invention therefore furthermore provides a switching and/or display device preferably comprising a smectic liquid-crystal mixture, which comprises one or more compounds of the formula (I).

Particular preference is given to switching and/or display devices comprising active matrix elements (cf. e.g. DE-A 198 22 830).

The present application cites various documents, for example in order to illustrate the technical background to the invention. All these documents are incorporated herein by reference.

The examples which follow illustrate the invention further without restricting it.

EXAMPLE 1

[4(5-Undecyl-pyrimidin-2-yl)phenyl] 5-propyl-tetrahydrothiophene-2-carboxylate 4.9 g of 4-(5-undecyl-pyrimidin-2-yl)phenol, 2.6 g of 5-propyl-tetrahydrothiophene-2-carboxylic acid (prepared as shown in Scheme 1) and 3.1 g of dicyclohexylcarbodiimide are stirred for 24 h in 50 ml of dichloromethane at room temperature. Filtration, removal of the dichloromethane by distillation, purification by chromatography (silica gel; dichloromethane/heptane) and recrystallization from acetonitrile affords the target compound as colorless crystals.

The compounds (I-1) to (I-12) can be obtained in a similar manner.

EXAMPLE 2

(5-Propyl-tetrahydrothiophen-2-yl)methyl [4(5-undecyl-pyrimidin-2-yl)phenyl]ether A fully reacted mixture of equimolar amounts of diethyl azodicarboxylate and triphenylphosphine in THF is admixed with equimolar amounts of 4-(5-undecyl-pyrimidin-2-yl) phenol and 5-propyl-tetrahydrothiophen-2-yl-methanol (prepared by LiAIH$_4$ reduction of methyl 5-propyl-tetrahydrothiophene-2-carboxylate). The mixture is stirred for 24 h at room temperature and then evaporated to dryness under reduced pressure. Purification by chromatography (silica gel, dichloromethane) and recrystallization affords the target compound. The compounds (I-13) and (I-14) can be obtained in a similar manner.

What is claimed is:

1. A tetrahydrothiophene derivative of the formula (I)

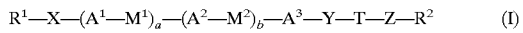

$$R^1—X—(A^1—M^1)_a—(A^2—M^2)_b—A^3—Y—T—Z—R^2 \quad (I)$$

where the symbols and indices have the following meanings:

T is undirected and is tetrahydrothiophene-2,5-diyl or tetrahydrothiophene-2,4-diyl $R^1$ is hydrogen or a straight-chain or branched $C_{1-20}$-alkyl or $C_{2-20}$-alkenyl radical (with or without asymmetric carbon atoms), where
 a) one or two nonterminal CH$_2$ groups may be replaced, independently of one another, by —O— or —C(=O)—, with the proviso that two adjacent CH$_2$ groups cannot be replaced in the same way, and/or
 b) one CH$_2$ group may be replaced by —C≡C—, and/or
 c) one CH$_2$ group may be replaced by —Si(CH$_3$)$_2$—, cyclopropane-1,2-diyl, cyclobutane-1,3-diyl, cyclopentane-1,4-diyl, bicyclo[1.1.1]pentane-1,3-diyl or cyclohexane-1,4-diyl, and/or
 d) one or more H atoms may be replaced by F and/or CN,
 e) in the case of a branched alkyl or alkenyl radical containing asymmetric carbon atoms, the asymmetric carbon atoms have —CH$_3$, —OCH$_3$, —CF$_3$, F, CN and/or Cl as substituents or are incorporated into a 3- to 7-membered ring, in which, in addition, one or two non-adjacent CH$_2$ groups may be replaced by —O— and one CH$_2$ group non-adjacent to these groups may be replaced by —OC(=O)—;

$R^2$ is hydrogen or a straight-chain or branched alkyl radical (with or without asymmetric carbon atoms) having 1 to 20 carbon atoms, where one nonterminal CH$_2$ group may be replaced by —O— or —OC(=O)— or —C(=O)O— and/or one or more H atoms may be replaced by F, with the provisos that
 a) the CH$_2$ group attached to Z cannot be replaced by —O— when Z is —O—
 b) $R^2$ can only be hydrogen when Z is a single bond and $R^1$ is not hydrogen X is a single bond, —O—, OC(=O)—, —C(=O)O— or —OC(=O)O—

Y is —OC(=O)—, —SC(=O)—, —OCH$_2$— or —CH$_2$CH$_2$—

Z is a single bond or —O—

$A^1$, $A^2$ and $A^3$ are undirected different and are each, independently of one another phenylene-1,4-diyl, unsubstituted or monosubstituted or disubstituted by CN or F, phenylene-1,3-diyl, unsubstituted or monosubstituted or disubstituted by CN or F, cyclohexane-1,4-diyl, in which one or two H atoms may be replaced, independently of one another, by CN, CH$_3$ or F, 1-cyclohexene-1,4-diyl, in which one H atom may be replaced by F, 1-alkyl-1-silacyclohexane-1,4-diyl, pyridine-2,5-diyl, unsubstituted or monosubstituted by F, pyrimidine-2,5-diyl, unsubstituted or monosubstituted by F, thiophene-2,5-diyl or (1,3,4)-thiadiazol-2,5-diyl $M^1$ and $M^2$ are undirected and are each, independently of one another —OC(=O)—, —OCH$_2$—, —CH$_2$CH$_2$—, —OC(=O)CH$_2$CH$_2$—, —OCH$_2$CH$_2$CH$_2$—, —C≡C—, —CH$_2$CH$_2$CH$_2$CH$_2$— or a single bond;

a and b are each, independently of one another, 0 or 1.

2. A liquid-crystal mixture comprising at least one compound of the formula (I) as claimed in claim 1.

3. A liquid-crystal mixture as claimed in claim 2, which is chiral smectic.

4. A liquid-crystal mixture as claimed in claim 2, which is nematic.

5. A liquid-crystal mixture as claimed in claim 2, which comprises from 0.01 to 80% by weight of one or more compounds of the formula (I).

6. A switching or display device, which comprises a liquid-crystal mixture as claimed in claim 2.

7. A switching or display device as claimed in claim 6, which comprises active matrix elements and wherein the chiral smectic liquid-crystal layer forms a monostable-switching monodomain.

* * * * *